United States Patent [19]

Nicolas et al.

[11] Patent Number: 5,714,183
[45] Date of Patent: Feb. 3, 1998

[54] HYDROLYSIS OF THE GALACTOMANNANS OF COFFEE EXTRACT WITH IMMOBILIZED BETA-MANNANASE

[75] Inventors: Pierre Nicolas, Saint Legior; Eric Raetz, Lausanne; Sylviane Reymond, Epalinges; Jean-Luc Sauvageat, Lausanno, all of Switzerland

[73] Assignee: Nestec SA, Vevey, Switzerland

[21] Appl. No.: 418,240

[22] Filed: Apr. 6, 1995

[30] Foreign Application Priority Data

Apr. 7, 1994 [EP] European Pat. Off. ............. 94105366

[51] Int. Cl.$^6$ .................................................. A23F 5/00
[52] U.S. Cl. .................. 426/45; 426/44; 426/330.3; 426/590; 426/594
[58] Field of Search .................... 426/45, 44, 590, 426/594, 595, 425, 431, 432, 629, 655, 330, 330.3

[56] References Cited

U.S. PATENT DOCUMENTS 2,801,920  8/1957  Reich et al. .................. 99/71

FOREIGN PATENT DOCUMENTS 2231319  12/1974  France .
2063489   6/1972  Germany .
1465168   2/1977  United Kingdom .

OTHER PUBLICATIONS

Chemical Abstracts, vol. 88, No. 7, 1978, Columbus, Ohio, US; Abstract No. 48996, J. Puls et al. "hydrolysis of Hemicelluloses by Immobilised Enzymes" & Trans. Tech. Sect., Can. Pulp Pap. Asoc., vol. 33, No. 3, 1977, pp. TR64—TR72.

Database WPI 27 Jul. 1993, Derwent Publications Ltd., London, GB; AN 93-360092 & BR-A-9 2000 186 (Embraba Empresa Brasil Pesquisa).

Database WPI 23 Nov. 1983, Derwent Publications Ltd., London, GB; AN 84-187394 & SU-A-1 055 770 (Baltsere D Yu).

Primary Examiner—Leslie Wong
Attorney, Agent, or Firm—Pennie & Edmonds

[57] ABSTRACT

Hydrolysis of the galactomannans of a liquid coffee extract, in which this extract is hydrolyzed at a temperature of 20°–80° C. with immobilized beta-mannanases.

19 Claims, 4 Drawing Sheets

HYDROLYSIS OF THE GALACTOMANNANS OF COFFEE EXTRACT WITH IMMOBILIZED BETA-MANNANASE

TECHNICAL FIELD

The present invention relates to a method of hydrolysis of the galactomannans contained in a liquid coffee extract.

BACKGROUND ART

U.S. Pat. No. 2,802,920 discloses the hydrolysis of galactomannans contained in a coffee extract with a preparation of beta-mannanases in order to prevent the formation of a gel during freezing of this extract.

Food Review, 8/9, 37–39 (1984) discloses the industrial use of beta-mannanases to decrease the viscosity of a liquid coffee extract, making it possible to concentrate it to high contents of dry matter.

However, this industrial use of beta-mannanases has certain drawbacks. For instance, the enzyme is wasted as it is used only once. The presence of enzyme in the final product is also undesirable.

The present invention is intended to remedy the drawbacks of the prior art.

SUMMARY OF THE INVENTION

The present invention relates to a method of hydrolysis of the galactomannans of a liquid coffee extract wherein the extract is hydrolyzed at a temperature of, e.g., 20°–80° C. with immobilized beta-mannanases.

The beta-mannanases are preferably immobilized by covalent bonding on a substrate or by polymerisation of the beta-mannanases adsorbed on a substrate.

The invention is therefore advantageous in that a saving of enzymes is achieved.

A further advantage lies in the fact that there is no salting out of the beta-mannanase from the substrate.

A further advantage lies in the fact that it is possible to work at a temperature such that no bacterial contamination is observed.

A surprising advantage of the present invention lies in the fact that the beta-mannanases do not lose their activity following their covalent bonding on a substrate or following polymerisation of the molecules adsorbed on a substrate. Similarly, the enzyme activity of the immobilized beta-mannanase is relatively constant over time.

Lastly, the present invention has the further advantage that the coffee extract may be hydrolyzed in a reactor of the stirred tank type, and in a reactor comprising a fixed bed or a fluidized bed of immobilized beta-mannanases, despite the viscosity of the coffee extract.

DETAILED DESCRIPTION OF THE PREFERRED EMBODIMENTS

In the following description, the term "reactor of the stirred tank type" is intended to mean a system which is mechanically stirred comprising immobilized beta-mannanases in suspension.

Similarly, the term "a fixed bed of immobilized beta-mannanases" is understood as beta-mannanases immobilized on or in a substrate which is compacted in a reactor adapted for the continuous processing of a liquid coffee extract.

The term "a fluidized bed of immobilized beta-mannanases" is understood as beta-mannanases immobilized on a substrate, which is disposed but not compacted in a reactor adapted for the continuous processing of a liquid coffee extract. The flow of coffee extract, circulating from the bottom to the top, then places the substrate particles in suspension. This type of reactor known as a "fluidized bed reactor" is particularly advantageous for the processing of mediums comprising solid matter in suspension.

The terms "mannobiose" and "mannotriose" respectively mean a dimer or a trimer of mannose, and the term "mannosaccharide" is understood as a polymer of at least two mannoses.

The unit of beta-mannanase is defined as the quantity of beta-mannanase which releases, from carob gum, a quantity of reducing sugars equivalent to one micromole of mannose per minute, at pH 5 and at 30° C.

The term "substantially free of beta-mannanase" means that the final product contains as little beta-mannanase as possible, and preferably none.

In order to carry out the invention, the beta-mannanase may therefore be immobilized by covalent bonding on the surface of a traditional substrate, or may also be immobilized by polymerisation of the beta-mannanase previously adsorbed on the surface of a traditional substrate, for instance.

The liquid coffee extract may then be hydrolyzed at a preferred temperature of 40°–70° C. with these enzymes immobilized, for instance.

For this purpose, use is preferably made of a bacterial or fungal beta-mannanase, in particular the beta-mannanase extracted from *Aspergillus niger*, in particular the purified beta-mannanase of *Aspergillus niger* marketed under the trademark Gamanase® (NOVO-NORDISK, Denmark), for instance.

Moreover, the liquid coffee extract may be obtained by percolating an extraction fluid through cells filled with ground roast coffee. This extraction may be carried out as a counter-current, i.e. water, under pressure at a temperature that may be between 150° and 180° C., is introduced into the cell containing the ground roast coffee charge that has been the most spent having undergone N extractions, at the base thereof. The liquid extract from this extraction cell is then caused to pass through the extraction cell containing the coffee charge that has been used (N−1) times and so on until the liquid extract passes through the cell which has just been filled with fresh ground roast coffee. The final extract that is used comes from the last cell at a temperature of approximately 100° C. It is possible therefore to distinguish between a pressurized stage, formed by the cells which contain the most spent coffee, and an atmospheric stage, formed by the cells which contain the least spent coffee.

The liquid coffee extract may also be obtained by percolating an extraction fluid through the cells filled with ground roast coffee of a pressurized stage. In this process, known as "split extraction", which term will be used in the remainder of the description, two extraction fluids are used, the extraction cells being divided into a pressurized stage and an atmospheric stage, each stage being extracted with its own extraction fluid. The coffee contained in the atmospheric stage is extracted with a first extraction fluid under moderate temperature and pressure conditions, while the coffee contained in the pressurized stage is extracted with a second extraction fluid at much higher temperature and pressure conditions. This consequently produces two different liquid extracts which, after partial evaporation of the extract from the pressurized stage, for instance, may be combined with one another and then converted into powder by conventional methods.

In the present invention, use may therefore be made, in particular, of the extract from the pressurized stage resulting from a split extraction of ground roast coffee, before the latter has been partially evaporated.

Use is therefore preferably made, of the extract from the pressurized stage disclosed in EP 0 538 512, for instance. According to the present invention, the substrate may also be a porous substrate, in particular having pores of a size of 20–200 nm, for instance.

In particular, the porous substrate may be chosen from the group formed by particles of silica, glass, an acrylic polymer, in particular the acrylic polymer Eupergit-C® (R ohm, Germany), and a phenolic polymer, in particular a phenol-formaldehyde resin Duolite® (Supelco, USA), in particular the resin Duolite® S-761, for instance.

The beta-mannanase is preferably immobilized by covalent bonding on the surface of the acrylic polymer Eupergit-C®. The latter has oxirane groups whose epoxy cycle makes it possible to immobilize the beta-mannanases. It is therefore possible to immobilize at least 1900 units of beta-mannanases per g of Eupergit-C®, for instance.

The beta-mannanases are preferably immobilized by polymerisation of the beta-mannanases adsorbed on the surface of particles of a phenolic resin Duolite®. It is possible, for instance, to use glutaraldehyde as a polymerisation agent.

In a first preferred embodiment of the present invention, the coffee extract is hydrolyzed in a reactor of the stirred tank type, with a beta-mannanase immobilized either by covalent bonding on a substrate or by polymerisation of the mannanases adsorbed on a substrate. The system may be automated and operate in a semi-continuous manner with the following three stages. In the first instance, the tank is filled with the coffee extract to be processed, then hydrolyzed with mechanical stirring, after which the tank is emptied after a predetermined period. The retention of the enzyme in the reactor may take place by means of a filter disposed in the lower portion of the tank. This filter may retain all the particles of a diameter greater than 40 μm, for instance.

According to this method of hydrolysis, it can be seen that the beta-mannanases immobilized by covalent bonding on a substrate have good stability, as they may conserve over 60% of their enzyme activity after at least 500 successive cycles of hydrolysis of coffee extracts, for instance.

In a second preferred embodiment of the present invention, the liquid coffee extract is continuously hydrolyzed in a reactor comprising a fixed bed of beta-mannanases immobilized either by covalent bonding on a substrate or by polymerisation of the beta-mannanases adsorbed on a substrate. When used in this way, the immobilized beta-mannanases retain good stability, as they may conserve over 80% of their enzyme activity after more than 20 hours of continuous hydrolysis, for instance.

In a third preferred embodiment of the present invention, the liquid coffee extract is continuously hydrolyzed in a reactor comprising a fluidized bed of beta-mannanases immobilized by covalent bonding on a substrate.

EXAMPLES

The following examples illustrate the method of the present invention. In these examples, use has been made of the beta-mannanase marketed under the trademark Gamanase® which has a specific activity of 65000 units per g of proteins, and in some of these examples use has been made, as a model substrate, of a 2% mixture of soluble coffee in distilled water or a solution of galactomannans prepared from carob gum, which provide a very good illustration of the results that can be obtained with a coffee extract.

These examples are preceded by a chromatographic analysis of the extracts and a description of the drawings.
HPTLC chromatography The oligosaccharides present in a liquid coffee extract were determined qualitatively and quantitatively by chromatography, without having to carry out a preliminary purification of this extract. It was thus possible to use this method in different tests, such as the enzyme kinetics of hydrolysis of galactomannans and the measurement of the residual enzyme activity of the hydrolyzed coffee extracts, for instance.

For this purpose, use was made of silica plates for HPTLC chromatography "silica gel 60" (Merck 5631/5641). The equivalent of 80 μg of dry coffee extract was deposited and three successive developments were carried out with a solvent composed of chloroform, acetic acid and water in proportions of 30/35/11. The plate was exposed at 110° C. for 30 minutes with a reagent comprising 4 ml of aniline, 4 g of diphenylamine, 200 ml of acetone and 30 ml of 85% phosphoric acid.

It was thus possible qualitatively to determine the oligosaccharides present in the extract, for instance free mannose, mannobiose, mannotriose and the other mannosaccharides having degrees of polymerisation lower than 8.

It was also possible to determine the content of the various oligosaccharides in the extract, by relating the density of a stain on the plate corresponding to an oligosaccharide of the extract and that corresponding to this oligosaccharide deposited on the plate at a known concentration. It was also considered that 100% hydrolysis of the galactomannans had been achieved when only mannobiose and mannotriose remained, as these are the reaction end products that the enzyme is no longer able to divide.

EXAMPLE 1

The beta-mannanase was immobilized by adsorption and polymerisation in a phenolic polymer, as follows. Use was made of the resin Duolite® S-761 (Supelco, USA) having pores of a size of approximately 60 nm. This resin was screened to obtain particles of 0.2–0.4 millimetres, processed with 0.5 N NaOH for one hour, then washed with water, then processed for 30 minutes with 0.25 N HCl and finally washed with distilled water to a pH of 4.25 ml of a solution composed of 5 ml of Gamanase® and 20 ml of 0.1 M sodium phosphate buffer of pH 6 were added to 5 g of processed resin, and the Gamanase® was left to adsorb on the resin for 12 hours at 22° C. with gentle stirring. The preparation was then washed with distilled water, and the adsorbed enzymes were polymerised by a solution of 2.5% of glutaraldehyde for 3 hours at 22° C. after which the preparation was finally washed with distilled water.

A solution of galactomannans was also prepared by heating 3 g of carob gum to 80° C. in 1 litre of 0.1 M acetate buffer of pH 5 and the soluble portion was used for the following tests.

The immobilized enzyme was thus tested in a conventional fixed bed reactor. This reactor comprised a tubular glass body, and two nylon filters (70 µm) maintaining a horizontal surface at each end of the body. The reactor was immersed in a water bath at 30° C. and the solution of galactomannans was pumped by a conventional peristaltic pump, then heated to 30° C. before passing through the reactor.

Figure 1A:
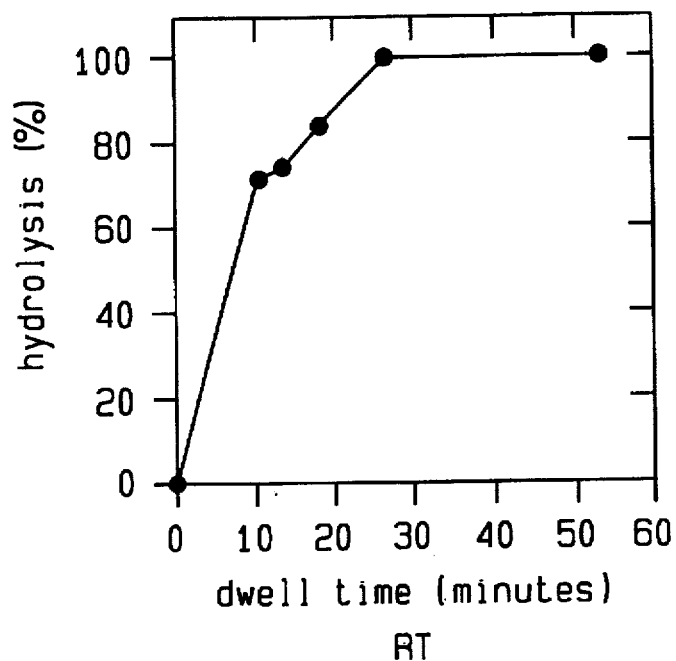
FIG. 1 (a and b): hydrolysis of galactomannans in a fixed bed reactor containing a beta-mannanase immobilized on Duolite® S-761. Representation of the percentage hydrolysis as a function of the dwell time (1a), and of the relative activity of the enzyme as a function of time (1b).

In the first instance, the solution of galactomannans was pumped at different speeds into the reactor. A conventional method was then used to measure the quantity of reducing sugars appearing in the eluate as a function of the dwell time (RT) of the extract in the reactor. The percentage hydrolysis of the galactomannans as a function of the dwell time of the extract in the reactor was then determined. It was considered that a 100% hydrolysis rate had been achieved when the quantity of reducing sugars produced was equal to that obtained, in a separate test, by total hydrolysis of the substrate with non-immobilized Gamanase®. The results are given in FIG. 1a.

Figure 1B:
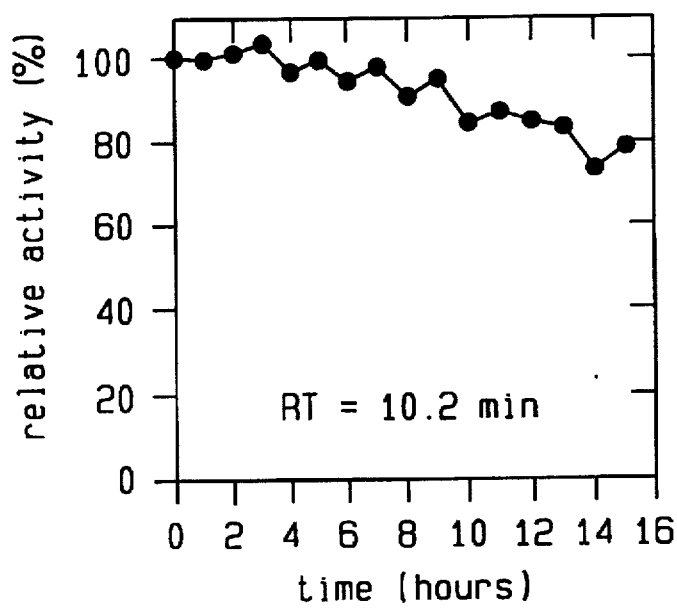

In the second instance, a solution of galactomannans was caused to pass continuously into the reactor. A dwell time (RT) which provided a hydrolysis rate of less than 100% at the beginning of the experiment was chosen for this purpose. The quantity of reducing sugars appearing in the eluate was then measured regularly. It can be seen that this quantity decreased as a function of time, probably because of a loss of enzyme activity. It is for this reason that the relative activity (%) of the enzyme was determined as a function of time, by relating the quantity of reducing sugars obtained and the quantity present at the beginning of the test. The results are given in FIG. 1b.

The following table shows some characteristics of the substrate.

| Gamanase ® immobilized on Duolite ® S-761 | |
| --- | --- |
| Temperature (°C.) | 30 |
| Bed height (mm) | 19 |
| Bed volume (ml) | 2.15 |
| Proteins (mg/g of substrate) | 37.2 |

EXAMPLE 2

The beta-mannanase was immobilized by covalent bonding on silica balls X-030 LS (Sepracor, France) having a diameter of 0.1–0.3 millimetres and pores of a size of approximately 60 nm, as follows.

The silica balls were previously coupled with gamma-aminopropyltriethoxysilane, in the manner disclosed in the method of silanisation in an aqueous medium of H. H. Weetall (Methods in Enz., 44, 135–148, 1976). 5 g of silica balls treated with 50 ml of a 2.5% glutaraldehyde solution in a 0.1 M sodium phosphate buffer of pH 7 were treated for 1 hour under vacuum followed by 2 hours at atmospheric pressure. The particles were then successively washed with distilled water, a solution of 0.5 M NaCl and a 0.1 M sodium phosphate buffer of pH 6. 25 ml of a solution comprising 5 ml of Gamanase® and 20 ml of sodium phosphate buffer of pH 6 were then added to the activated substrate, then left to act at 4° C. for 12 hours under a helium atmosphere. The balls were finally washed copiously with distilled water, then with a 0.1 M sodium phosphate buffer of pH 6.

Figure 2A:
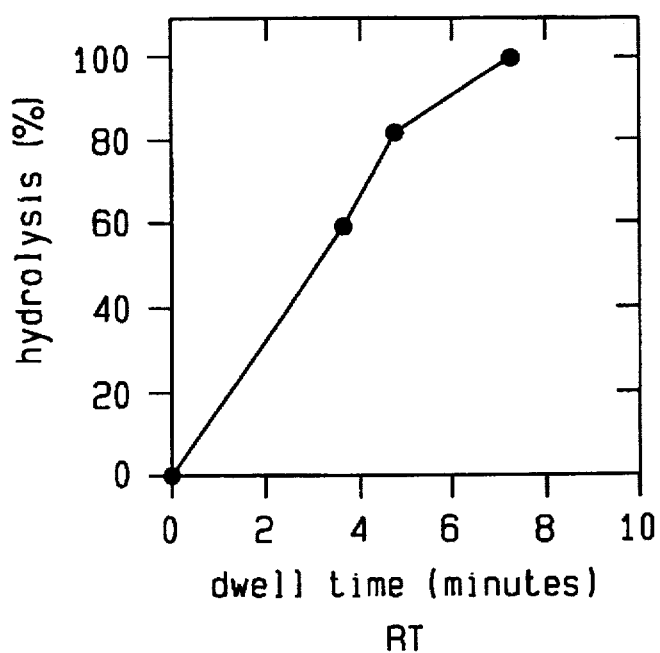
FIG. 2 (a and b): hydrolysis of galactomannans in a fixed bed reactor containing a beta-mannanase immobilized on silica balls. Representation of the percentage hydrolysis as a function of the dwell time (2a), and of the relative activity of the enzyme as a function of time (2b).
Figure 2B:
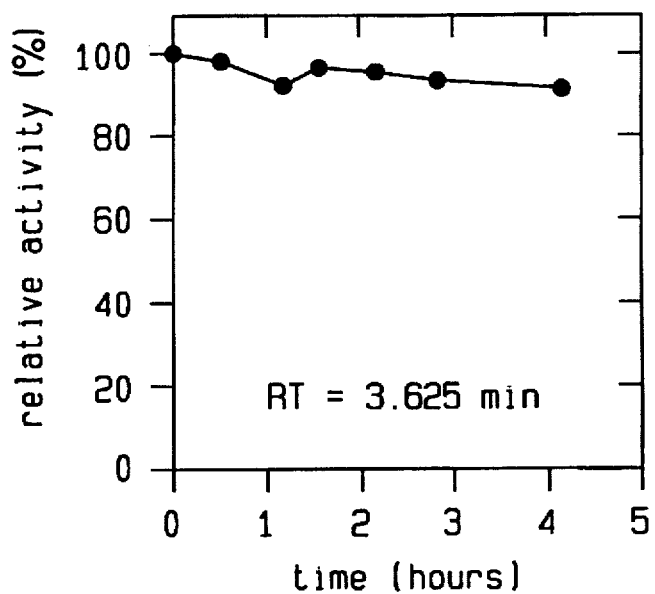

This preparation was then tested in the fixed bed reactor in the same way as in Example 1. The percentage hydrolysis of the galactomannans as a function of the dwell time of the substrate in the reactor was thus determined (FIG. 2a), as well as the relative activity of the enzyme as a function of time (FIG. 2b).

The following table illustrates some characteristics of the substrate used.

| Gamanase ® immobilized on silica balls X-030 LS | |
| --- | --- |
| Temperature (°C.) | 30 |
| Bed height (mm) | 20 |
| Bed volume (ml) | 2.26 |
| Proteins (mg/g of substrate) | 34.4 |

EXAMPLE 3

The beta-mannanase was immobilized by covalent bonding on Eupergit-C® acrylic polymer balls (Rohm, Germany) having pores of a size of approximately 35 nm and reactive oxiran groups, as follows.

37.5 ml of a solution composed of 7.5 ml of Gamanase® and 30 ml of 0.5 M potassium phosphate buffer of pH 7 was added to 5 g of Eupergit-C® and left to act with gentle stirring for 48 hours at ambient temperature. The preparation was then washed with 0.5 M potassium phosphate buffer of pH 7.

Figure 3A:
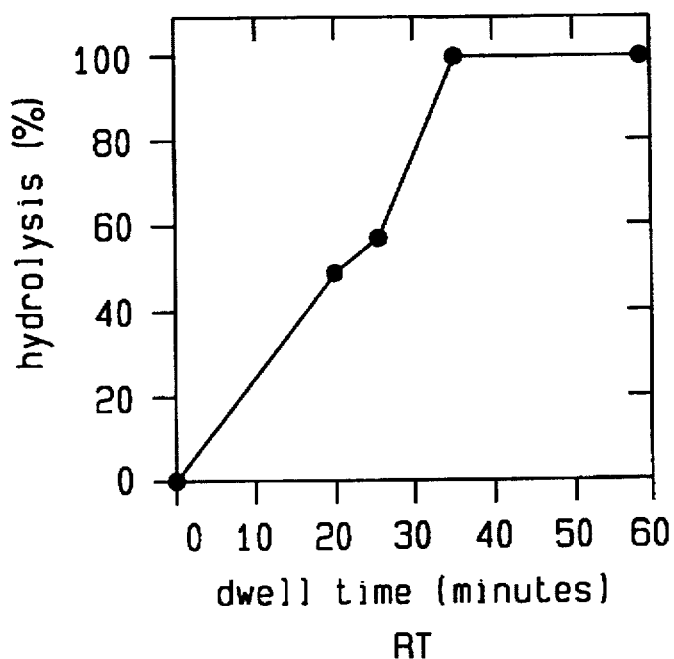
FIG. 3 (a and b): hydrolysis of galactomannans in a fixed bed reactor containing a beta-mannanase immobilized on Eupergit-C®. Representation of the percentage hydrolysis as a function of the dwell time (3a), and of the relative activity of the enzyme as a function of time (3b).
Figure 3B:
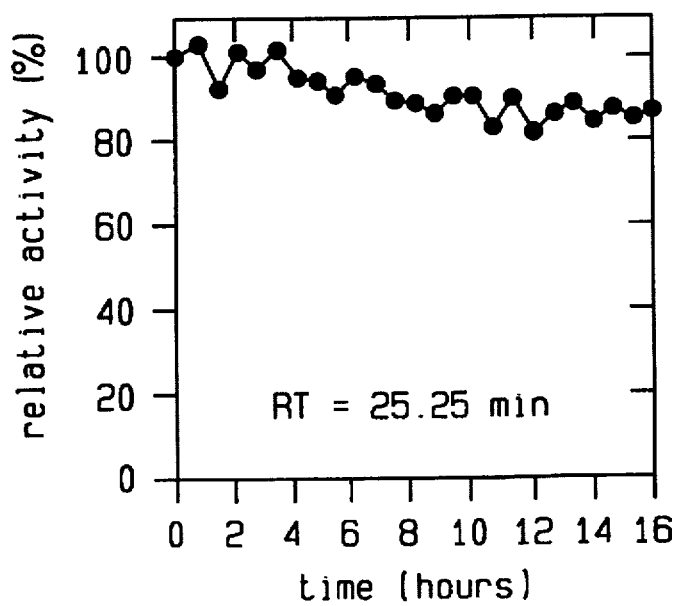

This preparation was then tested in the fixed bed reactor in the same way as described in Example 1. It was thus possible to determine the percentage hydrolysis of the galactomannans as a function of the dwell time of the substrate in the reactor (FIG. 3a) as well as the relative activity of the enzyme as a function of time (FIG. 3b). It can be seen that the stability of the enzyme was particularly good on this substrate as the immobilized beta-mannanase retained over 80% of its enzyme activity after 16 hours of continuous hydrolysis.

It can also be seen that no salting out of the enzyme from the substrate was observed in the eluate over time. When the eluate was incubated for several hours at 30° C. and changes in the content of reducing sugars were measured, there was no modification.

The following table shows some characteristics of the substrate used.

| Gamanase ® immobilized on Eupergit-C ® | |
| --- | --- |
| Temperature (°C.) | 30 |
| Bed height (mm) | 24 |
| Bed volume (ml) | 2.74 |
| proteins (mg/g of substrate) | 31.4 |

EXAMPLE 4

Immobilization was carried out by covalent bonding on 5 g of conventional glass particles with verified pores, having pores of a size of approximately 70 nm and also comprising aminopropyl groups (Sigma G5019), fixed in the same way as for the silica balls of Example 2.

This preparation was then tested in the fixed bed reactor described in Example 1, using a conventional soluble coffee extract (Nescafé®, Nestlé) at 2% in distilled water.

The rates of flow of the coffee extract were modified and the extract emerging from the reactor was analysed by HPTLC. It can be seen that for dwell times of 64 and 81 seconds, the reaction products were largely composed of mannobiose and mannotriose. Traces of oligomers containing 4 and 5 mannoses remained visible. When the dwell time was increased to 105 seconds, the only oligosaccharides present in the extract were mannobiose and mannotriose, showing a complete hydrolysis of the galactomannans.

The following table shows the characteristics of the substrate used.

| Gamanase ® immobilized on glass with verified pores | |
| --- | --- |
| Temperature (°C.) | 30 |
| Bed height (mm) | 15 |
| Bed volume (ml) | 1.69 |
| Proteins (mg/g of substrate) | 32.2 |

EXAMPLE 5

The liquid coffee extract from the pressurized stage resulting from the split extraction of ground roast coffee disclosed in Patent EP 0 538 512 was used to continuously supply the fixed bed reactor described in Example 1 which was kept at 50° C.

The reactor contained Gamanase® immobilized on Eupergit-C® in the manner described in Example 3. The flow rate was adjusted so as to obtain a dwell time of 8 minutes. Samples were regularly taken for 48 hours in order to evaluate the oligosaccharides produced by HPTLC chromatography.

There was a complete hydrolysis of the galactomannans of the extract, as the only oligosaccharides of the processed extract were mannobiose and mannotriose.

EXAMPLE 6

Several hydrolyses of the coffee extract described in Example 5 were carried out in a conventional vertical column comprising a fluidized bed of Gamanase® immobilized on Eupergit-C®.

The substrate comprised 28.6 mg of proteins per g of substrate, immobilized in a similar manner to that described in Example 3. The tests were carried out at 65° C.

Figure 4:
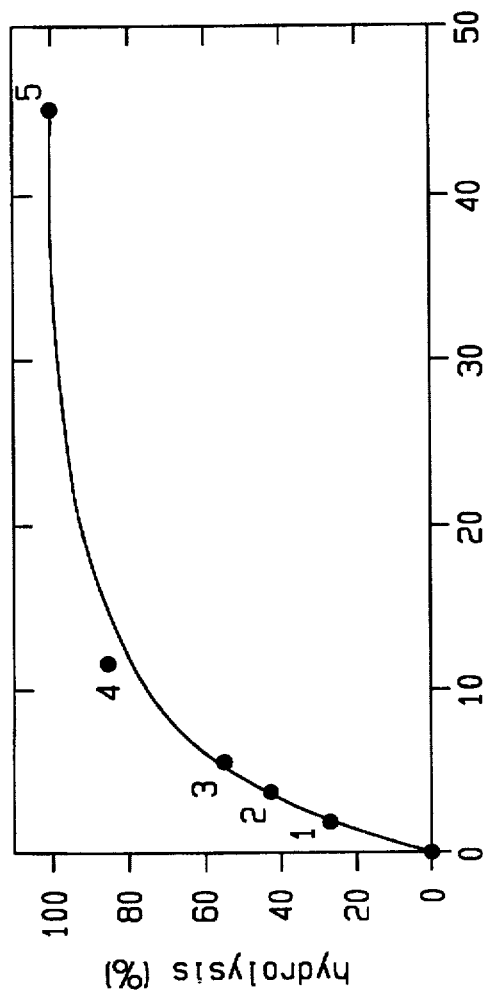
FIG. 4: hydrolysis of a coffee extract in a fluidized bed by a beta-mannanase immobilized on Eupergit-C®. Representation of the percentage hydrolysis as a function of the standardized dwell time.

The quantity of mannobiose present in the eluate of each test was then measured by the chromatographic method described above. The percentage hydrolysis of the galactomannans as a function of the standardised dwell time of the extract in the reactor (minutes×mg of proteins/ml) was then determined. FIG. 4 shows the results of these tests.

The experimental conditions of the various tests and the results obtained are shown in the following table.

| Test No. | Quantity of Eupergit-C ® (g/sec) | Flow (ml/h) | Standardised dwell time (min · mg/ml) | Hydrolysis (%) |
| --- | --- | --- | --- | --- |
| 1 | 1.31 | 1148 | 1.96 | 27.3 |
| 2 | 1.31 | 575 | 3.91 | 42.7 |
| 3 | 3.94 | 1180 | 5.73 | 54.7 |
| 4 | 3.94 | 585 | 11.6 | 85.5 |
| 5 | 3.94 | 150 | 45.1 | 100 |

EXAMPLE 7

Approximately 500 successive hydrolyses of the extract described in Example 5 were carried out in a tank of the stirred tank type comprising a suspension of Gamanase® immobilized on Eupergit-C®.

The enzymes were immobilized by adding 37.5 ml of a solution composed of 7.5 ml of Gamanase® and 30 ml of 1.25 M potassium phosphate buffer of pH 7 to 5 g of Eupergit-C®. This was left to act with gentle stirring for 72 hours at ambient temperature.

Each hydrolysis corresponded to a cycle of 30 minutes during which a pump introduced the extract into the tank for the first two minutes, the extract was left to react with stirring for the next 26 minutes and the pump suctioned the hydrolysed extract from the base of the tank during the final two minutes. The immobilized enzymes were retained by a filter (40 μm) placed at the base of the tank, the tank was thermostat-controlled to 60° C. and a portion of each eluate was analysed by the HPTLC chromatographic method described above. The density of the stains corresponding to mannobiose and mannotriose were then measured.

Figure 5:
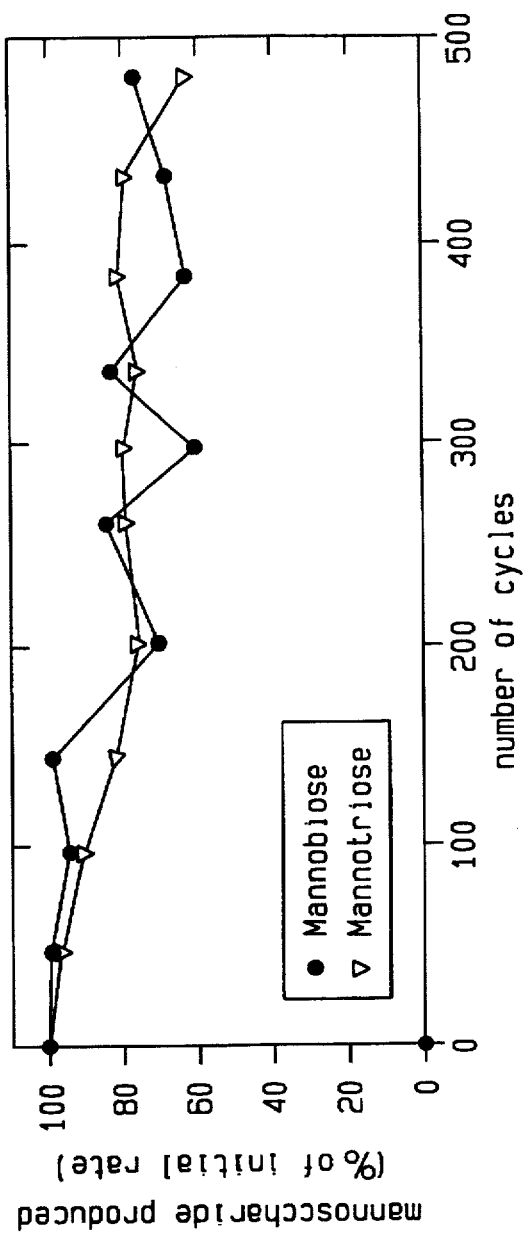
FIG. 5: hydrolysis of a coffee extract in a stirred tank by a beta-mannanase immobilized on Eupergit-C®. Representation of the percentage of mannosaccharide produced as a function of the number of hydrolysis cycles.

FIG. 5 shows the relative quantities of mannobiose and mannotriose produced as a function of the hydrolysis cycle number. It can be seen that the enzyme lost its enzyme activity particularly slowly, since the immobilized beta-mannanase retained over 60% of its enzyme activity after 500 successive cycles of hydrolysis of coffee extract.

No beta-mannanase activity is detectable in the final hydrolysis extract over the 500 successive cycles when tested by conventional chemical methods.

The experimental conditions are given in the following table.

| Gamanase ® immobilized on Eupergit-C ® Successive hydrolyses in a stirred tank | |
| --- | --- |
| Temperature (°C.) | 60 |
| Volume processed (ml) | 38 |
| Cycle duration (min) | 30 |
| Proteins (mg/g of substrate) | 47.3 |
| Wet immobilized enzyme (mg) | 400 |

As each example shows that no beta-mannanase is present in the final extract, the unexpected effectiveness of the present method has been demonstrated.

We claim:

1. A method for removing galactomannans from a liquid coffee extract which comprises hydrolyzing the extract with an immobilized beta-mannanase at a sufficient temperature and for a sufficient time to remove galactomannans from the extract and form a final product which is substantially free of beta-mannanase, wherein the immobilized beta-mannanase retains at least 60% of its enzyme activity after 500 cycles of hydrolyzing extracts.

2. A method as claimed in claim 1, in which the beta-mannanases are immobilized by covalent bonding on a substrate.

3. A method as claimed in claim 1, in which the beta-mannanases are immobilized by polymerisation of the mannanases adsorbed on a substrate.

4. A method as claimed in claim 1, in which the said extract is hydrolyzed at a temperature of between about 30°–70° C.

5. A method as claimed in claim 1, in which the beta-mannanase is a beta-mannanase extracted from *Aspergillus niger*.

6. A method as claimed in claim 1, in which the liquid coffee extract is the extract from the pressurized stage resulting from a split extraction of ground roast coffee.

7. A method as claimed in claim 1, in which the beta mannanase is immobilized on a porous substrate.

8. A method as claimed in claim 7, in which the pores of the substrate have a size of 20–200 nm.

9. A method as claimed in claim 7, in which the porous substrate is selected from the group consisting of silica, glass, an acrylic polymer and a phenolic polymer.

10. A method as claimed in claim 3, in which the beta-mannanase adsorbed on a substrate is polymerized by glutaraldehyde.

11. A method as claimed in claim 1, in which the liquid coffee extract is continuously hydrolyzed in a reactor comprising a fixed bed of immobilized beta-mannanases.

12. A method as claimed in claim 1, in which the liquid coffee extract is continuously hydrolyzed in a reactor comprising a fluidized bed of immobilized beta-mannanases.

13. A method as claimed in claim 1, in which the liquid coffee extract is hydrolyzed in a tank comprising immobilized beta-mannanases in suspension.

14. The method as claimed in claim 1 wherein the extract is hydrolyzed at a temperature of between about 20°–80° C.

15. The method as claimed in claim 1 wherein no beta-mannanase is detected in the final hydrolyzed product.

16. A method for removing galactomannans from a liquid coffee extract which comprises hydrolyzing such extracts with a beta-mannanase which is immobilized on a substrate at a temperature of between about 20° and 80° C. for a time sufficient to remove galactomannans from the extract and form a final product which is substantially free of beta-mannanase, wherein the immobilized beta-mannanase retains at least about 60% of its enzyme activity after 500 successive cycles of hydrolyzing the extracts.

17. The method of claim 16 wherein the beta-mannanase is immobilized on a porous substrate and each liquid coffee extract is obtained from a pressurized stage resulting from the split extraction of ground roast coffee.

18. The method of claim 17 wherein the substrate comprises particles of silica, glass, an acrylic polymer, or a phenolic polymer, and which further comprises immobilizing the beta-mannanase on the substrate particles by polymerization of the beta-mannanase thereon.

19. The method of claim 18 which further comprises polymerizing the beta-mannanase on the substrate particles by adsorbing the beta-mannanase onto the particles and treating the resulting particles with glutaraldehyde at a sufficient temperature and for a sufficient time to polymerize the beta-mannanase onto the substrate particles.

* * * * *